US005534009A

United States Patent [19]

Lander

[11] Patent Number: 5,534,009
[45] Date of Patent: Jul. 9, 1996

[54] TROCAR ASSEMBLY WITH ROTATABLE TIP

[75] Inventor: Jack R. Lander, Danbury, Conn.

[73] Assignee: United States Surgical Corporation, Norwalk, Conn.

[21] Appl. No.: 8,419

[22] Filed: Jan. 25, 1993

Related U.S. Application Data

[63] Continuation of Ser. No. 401,496, Aug. 29, 1989, abandoned, which is a continuation of Ser. No. 108,153, Oct. 13, 1987, abandoned.

[51] Int. Cl.⁶ .................................. A61B 17/34
[52] U.S. Cl. ...................... 606/185; 604/164; 604/264
[58] Field of Search .................... 606/184, 185, 606/191; 604/44, 108, 109, 158, 164, 165, 169, 272–274; 30/151, 152, 366–368; 433/102, 141, 143

[56] References Cited

U.S. PATENT DOCUMENTS

| 2,803,877 | 6/1954 | Belanger | 30/317 |
| 3,713,447 | 1/1973 | Adair | 604/169 |
| 4,573,448 | 3/1986 | Kambin . | |
| 4,601,710 | 7/1986 | Moll . | |
| 4,654,030 | 3/1987 | Moll et al. . | |

FOREIGN PATENT DOCUMENTS

| 0238461 | 9/1987 | European Pat. Off. . |
| 8511787 | 8/1986 | Germany . |
| 8634674 | 4/1988 | Germany . |

Primary Examiner—Michael H. Thaler
Assistant Examiner—William W. Lewis

[57] ABSTRACT

A trocar assembly includes a hand grip and a trocar obturator. The trocar obturator includes a front end on which is mounted a piercing tip, and an opposite rear end. The trocar obturator is mounted on the hand grip at its rear end, and is adapted to rotate independently of the hand grip. A retaining head is mounted on the rear end of the obturator, and is rotatably but securely received by a socket formed in the hand grip.

13 Claims, 3 Drawing Sheets

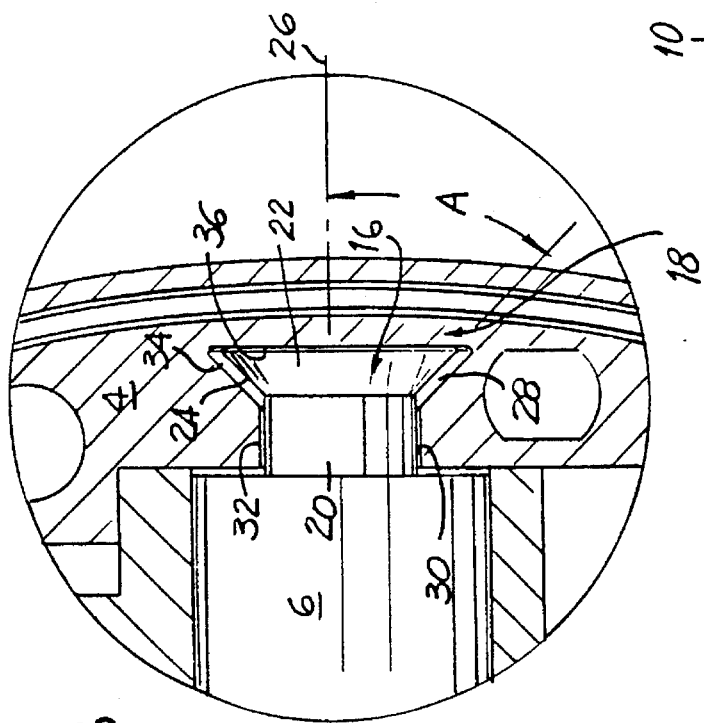
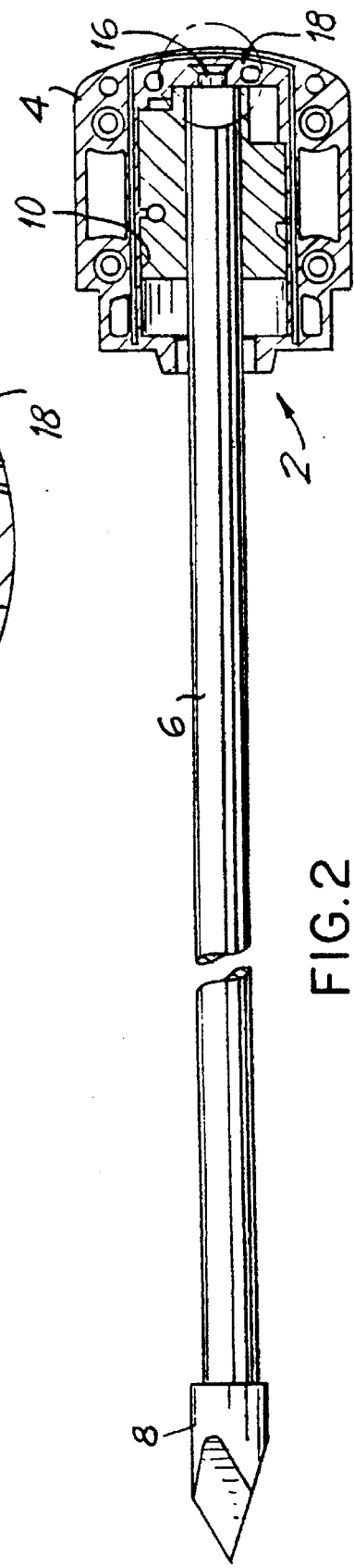
FIG.3
FIG.2

TROCAR ASSEMBLY WITH ROTATABLE TIP

This is a continuation of application Ser. No. 07/401,496 filed on Aug. 29, 1989, now abandoned, which is a continuation of U.S. Ser. No. 07/108,153 filed Oct. 13, 1987, now abandoned.

BACKGROUND OF THE INVENTION

1. Field of the Invention

The invention relates to a surgical instrument, and more particularly relates to a trocar assembly.

2. Description of the Prior Art

Trocars are basically sharp-pointed surgical instruments which are used to puncture a body cavity. This is often done so that fluids may be drained from the body cavity using a cannula inserted into the puncture opening, or the cavity may be examined using an endoscopic instrument in accordance with insufflatory surgical techniques.

Two conventional trocar assemblies are disclosed in U.S. Pat. No. 4,654,030, which issued to Frederic Moll et al. and in copending U.S. patent application Ser. No. 920,509 filed Oct. 17, 1986. The trocar assembly disclosed in the Moll et al. patent includes an obturator having a sharpened tip at one end for piercing a body cavity, and a hand grip portion mounted on the other end of the obturator which the surgeon grasps in the palm of his hand.

Conventional trocars have their obturators secured to the hand grip so that the obturator cannot rotate separately from the hand grip. For example, the trocar assembly disclosed in the Moll et al. patent has a triangular-shaped depression 32 formed in the hand grip 14, which depression receives the triangular-shaped end of the obturator to prevent the obturator from rotating relative to the hand grip during use.

It has been found that use of a trocar assembly in which the obturator cannot rotate independently of the hand grip may cause unnecessary trauma to the body cavity tissue, which would be avoidable if the obturator were rotatably mounted on the hand grip. This is because a considerable force is usually required to thrust the trocar through the body cavity wall. When applying this force, the surgeon very often will inadvertently twist or turn the trocar. The rotation of the trocar effects a grinding or drilling action of the obturator's piercing tip, which tears the tissues surrounding the puncture opening and traumatizes the wound.

OBJECTS AND SUMMARY OF THE INVENTION

It is an object of the present invention to provide a trocar assembly which minimizes trauma to the tissues surrounding the trocar puncture wound.

It is another object of the present invention to provide a trocar assembly which the surgeon can easily maneuver into the body cavity.

It is a further object of the present invention to provide a simple yet effective mechanism which joins the obturator to the hand grip of a trocar assembly but allows the obturator to freely rotate with respect to the hand grip.

It is yet another object of the present invention to provide a trocar assembly which overcomes the inherent disadvantages of conventional trocar assemblies having non-rotatable obturators.

In one form of the present invention, a trocar assembly basically includes a hand grip for the surgeon to grasp and a trocar obturator. The trocar obturator includes a front end and a rear end opposite the front end. A sharpened tip for piercing a body cavity is mounted on the front end of the obturator. The obturator is rotatably mounted on the hand grip at the obturator's rear end.

A retaining head is mounted on the rear end of the obturator. The retaining head is rotatably but securely mounted in a socket formed in the hand grip. The retaining head is disposed co-axially to the obturator, and includes a shank portion and an enlarged, frusto-conically shaped end portion mounted on the shank portion. The socket of the hand grip is shaped to conform to the shape of the retaining head so that it closely receives the retaining head and retains the obturator to the hand grip but allows the obturator to freely rotate independently of the hand grip.

Preferred forms of the trocar assembly, as well as other embodiments, objects, features and advantages of this invention, will be apparent from the following detailed description of illustrative embodiments thereof, which is to be read in connection with the accompanying drawings.

BRIEF DESCRIPTION OF THE DRAWINGS

FIG. 2 is a sectional view of one preferred embodiment of the trocar assembly shown in FIG. 1.

FIG. 3 is an enlarged, detailed view of a portion of the trocar assembly.

DETAILED DESCRIPTION OF THE PREFERRED EMBODIMENTS

Figure 1:
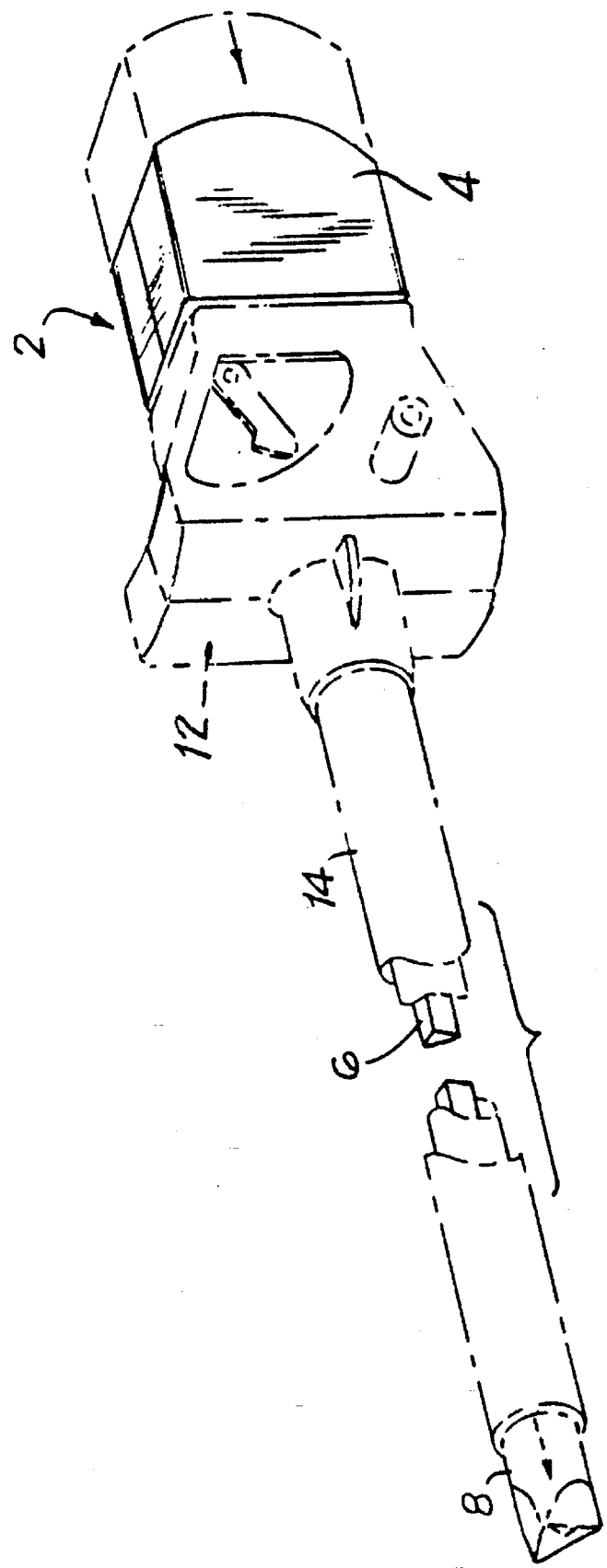
FIG. 1 is an isometric view of the trocar assembly of the present invention, in combination with a cannula assembly shown in phantom lines.

Referring initially to FIGS. 1 and 2 of the drawings, it will be seen that a trocar assembly 2 constructed in accordance with the present invention includes a hand grip portion 4, and an obturator 6 mounted on the hand grip portion 4.

The obturator 6 is basically an elongated shaft having a front end and an opposite rear end. The obturator 6 is provided with a sharpened tip 8 mounted on its front end, which tip is used for piercing the body cavity. The rear end of the obturator is mounted on the hand grip 4. The obturator 6 is preferably formed from stainless steel or glass reinforced plastic, or other material of suitable strength. The cutting tip 8 is also preferably formed from stainless steel or other material suitable for taking and holding a keen edge.

The hand grip 4 is basically formed from two mating halves which, when joined together, define a bore or cavity 10 for receiving the rear end of the obturator 6. The hand grip portion 4 is preferably formed from a plastic material, although other materials may be suitable for use.

The trocar assembly 2 is adapted to be received by a mating cannula assembly 12, such as shown in phantom lines in FIG. 1. The cannula assembly 12 includes a cannula 14 having opposite open ends through which the obturator 6 with its piercing tip 8 passes. A more detailed description of the cannula assembly and its operation is provided in U.S. Pat. No. 4,654,030 (Moll et el.), which is incorporated by reference herein.

As shown in FIGS. 2 and 3 of the drawings, the obturator 6 is rotatably mounted at its rear end on the hand grip portion 4 of the trocar assembly. The mechanism for mounting the obturator 6 on the hand grip 4 basically includes a retaining head 16, which retaining head is formed or mounted on the rear end of the obturator 6 and disposed co-axially to the obturator, and a socket 18 which is formed in the hand grip 4 and which receives the retaining head 16.

The retaining head 16, in its preferred form, includes a cylindrical shank 20 secured to the rear end of the obturator 6, and an enlarged end portion 22 mounted on the end of the shank 20. The end portion 22 has a greater diameter than that of the shank 20.

The end portion 22 of the retaining head is preferably formed with a frusto-conical shape and with a cross-section which widens in a direction outwardly from the rear end of the obturator 6, although the end portion 22 may be formed with other enlarged shapes to rotatably secure the obturator 6 to the hand grip 4. In the preferred form of the retaining head described above, the side wall 24 of the frusto-conically shaped end portion 22 preferably flares outwardly from the axis 26 of the obturator at an angle A of about 45°.

The socket 18 of the hand grip portion 4 is shaped to conform to the shape of the retaining head 16 and to allow the retaining head to rotate within the socket. It is thus preferably formed with a widened portion 28, which receives the end portion 22 of the retaining head, and a narrowed portion 30 of lesser diameter, which receives the shank 20 of the retaining head. When the obturator 6 is mounted on the hand grip 4 of the trocar assembly, the retaining head 16 is held captive in the socket 18.

More specifically, the narrowed portion 30 of the socket is defined by a cylindrical wall 32 which surrounds the shank 20 of the retaining head, and the widened portion 28 of the socket is defined by a conically-shaped side wall 34 of the hand grip, which wall slopes inwardly at substantially the same angle (i.e., 45°) as that of the retaining head's end portion 22, and by a circular back wall 36 which has a greater diameter than that of the end portion. This particular shape provides a slight gap between the socket 18 and the retaining head 16 so that the retaining head may freely rotate within the socket with little friction.

As mentioned previously, although the retaining head 16 is preferably formed with a frusto-conical shape, as shown in the drawings and described above, it is envisioned to be within the scope of the invention to provide the retaining head with various other shapes which secure the obturator 6 to the hand grip 4 of the assembly 2 but which allow the obturator to freely rotate with respect to the hand grip.

The trocar assembly 2 of the present invention is used in a well known manner, such as described in the Moll et al. U.S. Pat. No. 4,654,030. However, the advantage of the present invention over conventional trocar assemblies is that the obturator's piercing tip 8 will not turn when the surgeon thrusts the trocar through the wall of the body cavity, as the obturator tip is free to rotate independently of the hand grip portion 4 grasped by the surgeon. Thus, the surgeon is free to turn his wrist while piercing the body cavity using the trocar assembly without fear of causing unnecessary injury or trauma to the tissues surrounding the puncture wound.

Figure 4:
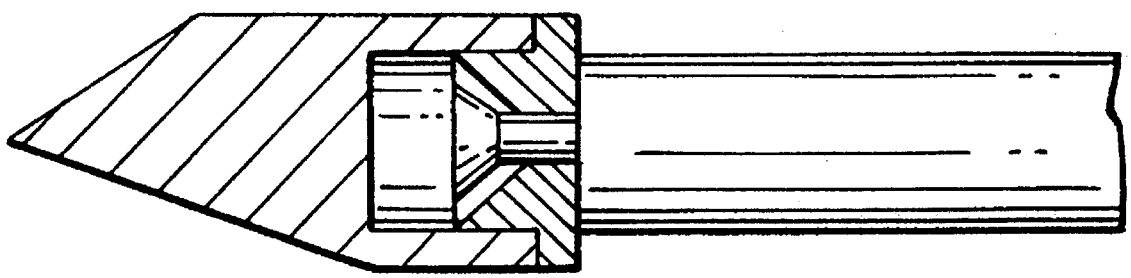
FIG. 4 is a sectional view of the front portion of an alternate embodiment of the trocar assembly shown in FIG. 1 wherein the piercing tip is rotatably attached to the obturator.

Although the trocar assembly described above includes an obturator 6 which rotates with respect to the hand grip portion 4, it is envisioned to form the assembly with a non-rotatable obturator secured to the hand grip, and a piercing tip portion which is rotatably mounted on the front end of the obturator as shown in FIG. 4. The mechanism which rotatably joins the tip portion to the rest of the obturator may be structured similarly to the retaining head 16 and socket 18 described previously. Either of these embodiments of the trocar assembly will minimize trauma to the tissues surrounding the puncture wound because each allows the obturator's piercing tip to rotate independently of the hand grip portion which is grasped by the surgeon.

The trocar assembly of the present invention overcomes the inherent drawbacks of conventional trocars with non-rotatable obturators. It minimizes trauma to the tissues surrounding the trocar puncture wound and can be easily maneuvered by the surgeon. The retaining head and socket arrangement is a simple yet effective mechanism for securing the obturator to the hand grip and for allowing the obturator and in particular the piercing tip to rotate independently of the hand grip.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A trocar assembly for piercing a body cavity which comprises:

hand gripping means dimensioned and configured to be held firmly between the palm and fingers of the user;

a trocar obturator having a front end portion and a rear end portion;

means for mounting said rear end portion of said trocar obturator on said hand gripping means;

a body piercing tip mounted on the front end portion of said trocar obturator and adapted for piercing a wall portion of the body cavity upon application of a predetermined force;

means to permit said body piercing tip to rotate independently of said hand gripping means such that when said hand gripping means is held firmly between the palm and the fingers of the user and said piercing tip is positioned against a body portion, and said piercing tip is thrust through the wall of the body cavity, said piercing tip is held in fixed position by the wall of the body cavity while said hand gripping means is permitted to rotate independent of said piercing tip;

an enlongated trocar tube dimensioned and configured for reception of said trocar obturator;

said obturator mounting means includes a retaining head mounted on the rear end of the obturator, the retaining head being rotably and securely mounted in a socket formed in the hand grip portion;

said retaining head is disposed co-axially to the obturator and includes a frusto-conically shaped end portion, the socket of the hand grip portion having a shape conforming to that of the retaining head end portion to closely receive and retain the end portion;

said frusto-conically shaped end portion has a cross-section which widens in a direction rearwardly from the rear end of the obturator.

2. A trocar assembly which comprises:

a) an elongated trocar obturator having a body piercing tip at a distal end thereof;

b) a cannula assembly including a cannula housing and an elongated trocar tube fixedly mounted to said cannula housing, said body piercing tip being configured and dimensioned to pass into and through said elongated trocar tube;

c) a hand grip mounted on the rear end of said obturator dimensioned and configured to mate with the cannula housing and to be grasped by a user; and d) means to permit said body piercing tip to rotate independently of said hand grip and said elongated trocar tube such that when said hand grip is grasped by a user and said piercing tip is positioned against a body wall, and said piercing tip is thrust through the body wall, said piercing tip is held in fixed position by the body wall at least until said piercing tip passes through the body wall, while said hand grip and said elongated trocar tube are permitted to rotate independent of said piercing tip.

3. A trocar assembly as defined by claim 2 wherein said body piercing tip includes a retaining head mounted on the front end of the obturator and disposed coaxially therewith.

4. A trocar assembly as defined by claim 3 wherein said retaining head has a frusto-conically shaped configuration.

5. A trocar assembly as defined by claim 4 wherein said frusto-conically shaped retaining head widens in a direction forwardly of the obturator.

6. A trocar assembly as defined by claim 5 wherein said body piercing tip defines a corresponding frusto-conically shaped socket dimensioned and configured to receive and retain said retaining head of said obturator while permitting rotation of said piercing tip relative to said obturator.

7. A trocar assembly which comprises:

a) an elongated trocar obturator having a body piercing tip at a distal end thereof, said piercing tip being rotatably mounted to said obturator;

b) a cannula assembly including a cannula housing and an elongated trocar tube fixedly mounted to said cannula housing, said body piercing tip being configured and dimensioned to pass into and through said elongated trocar tube;

c) a hand grip mounted on the rear end of said obturator and dimensioned and configured to mate with the cannula housing and to be grasped by a user, said body piercing tip rotating independently of said hand grip and said elongated trocar tube such that when said hand grip is grasped by a user and said piercing tip is thrust through a body wall, said piercing tip is held in a fixed position by the body wall at least until said piercing tip passes entirely through the body wall, while said hand grip and said elongated trocar tube are permitted to rotate independent of said piercing tip.

8. In combination:

a) a trocar assembly including a hand grip dimensioned and configured to be grasped by the user and an obturator rotatably mounted and extending from the said hand grip, said obturator having a body piercing tip at a distal end thereof; and b) a cannula assembly including a cannula housing and an elongated trocar tube fixedly mounted to and extending from said cannula housing, said piercing tip dimensioned to pass into and through said elongated trocar tube so as to extend beyond a distal end of said elongated trocar tube said piercing tip rotating independently of said hand grip and said elongated trocar tube.

9. The combination of claim 8 wherein said body piercing tip includes a retaining head extending from the distal end of the obturator and disposed coaxially therewith.

10. The combination of claim 9 wherein said retaining head has a frusto-conically shaped configuration.

11. The combination of claim 10 wherein said frusto-conically shaped retaining head widens in a direction forwardly of the obturator.

12. The combination of claim 11 wherein said body piercing tip defines a corresponding frusto-conically shaped socket dimensioned and configured to receive and retain said retaining head of said obturator while permitting rotation of said piercing tip relative to said obturator.

13. A method of puncturing a body wall comprising:

(i) providing a trocar assembly including:
  a) an elongated obturator having a body piercing tip at its front end, said body piercing tip being rotatably mounted to said obturator;
  b) a cannula assembly including a cannula housing and an elongated trocar tube fixedly mounted to said cannula housing;
  c) a hand grip mounted to the rear end of said obturator and dimensioned and configured to mate with said cannula housing and to be grasped by a user;

(ii) grasping at least said hand grip;

(iii) positioning said piercing tip against a body wall;

(iv) applying pressure to said hand grip to force said piercing tip through the body wall, said piercing tip being held in a fixed position by the body wall at least until said piercing tip passes entirely through the body wall, said hand grip and said elongated trocar tube being permitted to rotate independent of said piercing tip as pressure is applied.

* * * * *